United States Patent
Lee et al.

(10) Patent No.: US 10,323,223 B2
(45) Date of Patent: Jun. 18, 2019

(54) HOMOGENEOUS CELL DISPENSING MIXER

(71) Applicant: PBS Biotech, Inc., Camarillo, CA (US)

(72) Inventors: Chanyong Brian Lee, Thousand Oaks, CA (US); Yasunori Hashimura, Camarillo, CA (US); Oscar Garza, Camarillo, CA (US); Gary Evans, Camarillo, CA (US)

(73) Assignee: PBS Biotech, Inc., Camarillo, CA (US)

( * ) Notice: Subject to any disclaimer, the term of this patent is extended or adjusted under 35 U.S.C. 154(b) by 9 days.

(21) Appl. No.: 15/413,077

(22) Filed: Jan. 23, 2017

(65) Prior Publication Data

US 2017/0211031 A1      Jul. 27, 2017

Related U.S. Application Data

(60) Provisional application No. 62/286,294, filed on Jan. 22, 2016.

(51) Int. Cl.
| | |
|---|---|
| *C12M 1/00* | (2006.01) |
| *C12M 1/06* | (2006.01) |
| *C12N 5/071* | (2010.01) |
| *C12M 1/26* | (2006.01) |
| *C12M 1/12* | (2006.01) |

(52) U.S. Cl.
CPC ........... *C12M 27/06* (2013.01); *C12M 33/04* (2013.01); *C12M 37/00* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,245,555 | B1 * | 6/2001 | Curtis | C12M 23/26 220/495.05 |
| 7,198,940 | B2 * | 4/2007 | Vellinger | C12M 27/10 435/286.5 |
| 8,822,208 | B2 * | 9/2014 | Chokshi | C12M 23/08 435/288.6 |
| 8,999,702 | B2 * | 4/2015 | Kelly, Jr. | C12M 23/20 435/289.1 |
| 9,932,553 | B2 * | 4/2018 | Brau | B01F 13/0272 |
| 2008/0261299 | A1 * | 10/2008 | Zeikus | C12M 27/06 435/289.1 |
| 2008/0268530 | A1 * | 10/2008 | Zeikus | B01F 3/04588 435/289.1 |
| 2008/0274541 | A1 * | 11/2008 | Selker | B01F 3/04248 435/289.1 |
| 2009/0269849 | A1 * | 10/2009 | Lee | B01F 3/04588 435/383 |
| 2013/0288346 | A1 * | 10/2013 | Tuohey | C12M 23/26 435/287.1 |
| 2015/0103617 | A1 * | 4/2015 | Dujardin | C12M 23/26 366/102 |

(Continued)

*Primary Examiner* — Brian R Gordon
(74) *Attorney, Agent, or Firm* — SoCal IP Law Group LLP; Guy L. Cumberbatch

(57) ABSTRACT

A vessel having a mixer that ensures a homogeneous cell distribution in dispensed quantities. The vessel has a mixer therein for stirring contents of the vessel and an orifice in a lower wall to which a cell dispenser is attached. The cell dispenser dispenses quantities of suspended cells having a homogeneous cell distribution.

17 Claims, 2 Drawing Sheets

(56) References Cited

U.S. PATENT DOCUMENTS

| | | | |
|---|---|---|---|
| 2015/0118753 A1* | 4/2015 | Brau | B01F 13/0272 |
| | | | 435/394 |
| 2015/0175951 A1* | 6/2015 | Lee | C12M 23/28 |
| | | | 435/295.1 |
| 2015/0258513 A1* | 9/2015 | Morrissey | C12M 23/14 |
| | | | 366/265 |
| 2016/0296897 A1* | 10/2016 | Marshall | B01F 7/00091 |
| 2017/0267962 A1* | 9/2017 | Khan | C12M 27/02 |
| 2017/0320027 A1* | 11/2017 | Morrissey | B01F 7/00241 |
| 2017/0369828 A1* | 12/2017 | Mietzner | C12M 23/02 |
| 2018/0043322 A1* | 2/2018 | Morrissey | B01F 7/00241 |
| 2018/0071700 A1* | 3/2018 | Staheli | B01F 7/00058 |
| 2018/0078911 A1* | 3/2018 | Marshall | B01F 7/00091 |
| 2018/0117546 A1* | 5/2018 | Hurd | B01F 3/0412 |

\* cited by examiner

HOMOGENEOUS CELL DISPENSING MIXER

RELATED APPLICATIONS

The present application claims priority under 35 U.S.C. § 119 to U.S. Provisional Application No. 62/286,294, filed Jan. 22, 2016.

TECHNICAL FIELD

The invention pertains to vessels for dispensing cultured cells suspended in fluid and, more particularly, to a vessel having a mixer for dispensing quantities of cells suspended in fluid having a homogeneous cell distribution.

BACKGROUND OF THE INVENTION

In the conventional therapeutic protein-based industry, recombinant cells are expanded and induced to produce target proteins, which are then isolated and purified before final formulation in chilled excipient designed to stabilize proteins. In such application, maintaining proteins in uniform suspension in the final fill/finish step is not a great concern, largely due to the fact that proteins do not settle very fast in the excipient relative to the time required for processing to create noticeable concentration gradient.

On the other hand, in the growing field of cell therapy where animal cells in their native pluripotent, induced pluripotent, and/or differentiated form would be cultured and expanded, the cells themselves are the final product that must be isolated and dispensed into final vials. Maintaining cells in uniform suspension in the excipient during the dispensing step is more critical and challenging compared to maintaining proteins in suspension. Although there are a number of ways to dispense such cells in the art, such as withdrawing cells with a pipette from above, none as yet has been able to repeatedly and accurately dispense cultured cells from a vessel on demand.

SUMMARY OF THE INVENTION

The present application discloses a vessel having a mixer that ensures a homogeneous cell distribution in dispensed quantities.

An appreciation of the other aims and objectives of the present invention and an understanding of it may be achieved by referring to the accompanying drawings and the detailed description of the preferred embodiment.

DESCRIPTION OF THE PREFERRED EMBODIMENTS

The present application relates to vessels for dispensing cells suspended in fluid and, more particularly, to a vessel having a mixer that ensures a homogeneous cell distribution in dispensed quantities.

In the growing field of cell therapy the final products are animal cells in their native pluripotent, induced pluripotent, and/or differentiated form. The cells themselves must be isolated and dispensed into final vials. Maintaining cells in uniform suspension in the excipient during the dispensing step is much more critical and challenging compared to maintaining proteins in suspension. This is due to the faster settling velocity of cells, the relatively large size of the cells (micrometer scale vs. nanometer scale) which limits the minimum size of the orifice required for accurate and low-shear dispensing, and the higher shear sensitivity level of cells which can impact the viability of cells dispensed.

Further, the cell-dispensing step requires that a sterile vessel be used to mix the animal cells and excipient at a controlled refrigeration (2-8° C.) temperature and in an aseptic manner to ensure that the cell product is not contaminated with foreign particles or microorganisms. Typical lot release criteria for this cell-dispensing step are that the vials selected for QC inspection must meet a target cell concentration that fall within acceptable tolerance and that they must meet a minimum viability target. The process requires that cells be dispensed in accurate volume, at accurate cell concentration, within short processing time, and at controlled 2-8° C. temperature to ensure uniformity in cell concentration and high cell viability in the vials.

This proposed solution for dispensing such animal cells includes a vessel for containing the cell suspension having a mixing device that allows the cells to be maintained in uniform suspension during dispensing at 2-8° C. condition into vials in a relatively low-shear manner to avoid damaging cells. The device would consist of a mixing vessel to hold the cells and excipient in a sterile manner, with an impeller that is rotated by any number of means—pneumatically, magnetically, or otherwise—to keep the cells suspended uniformly in the excipient. The rotational speed of the impeller should be controllable by the user in a repeatable manner and to the extent that would allow the cells to be suspended uniformly and dispensed within allowable tolerance.

Figure 1:
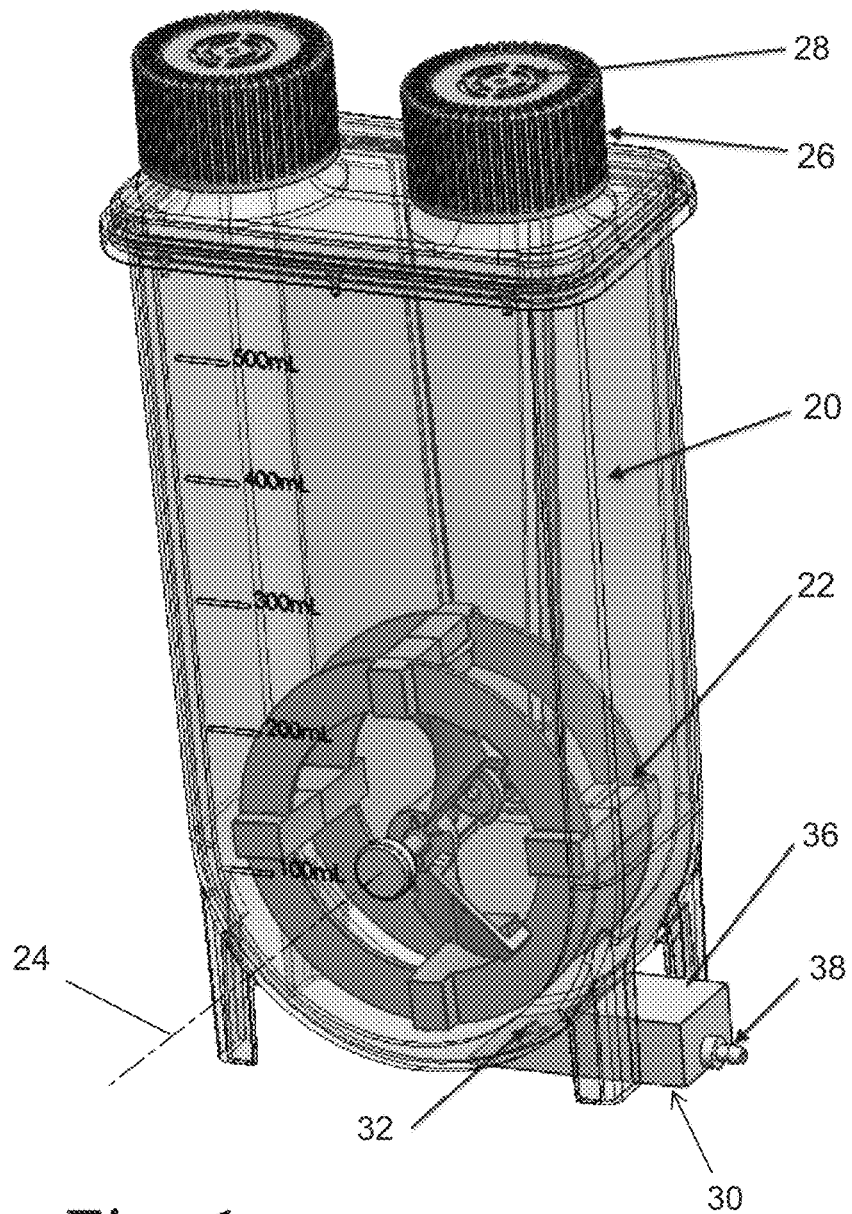
FIG. 1 is a perspective view of an embodiment of the homogeneous cell-dispensing mixer.
Figure 2:
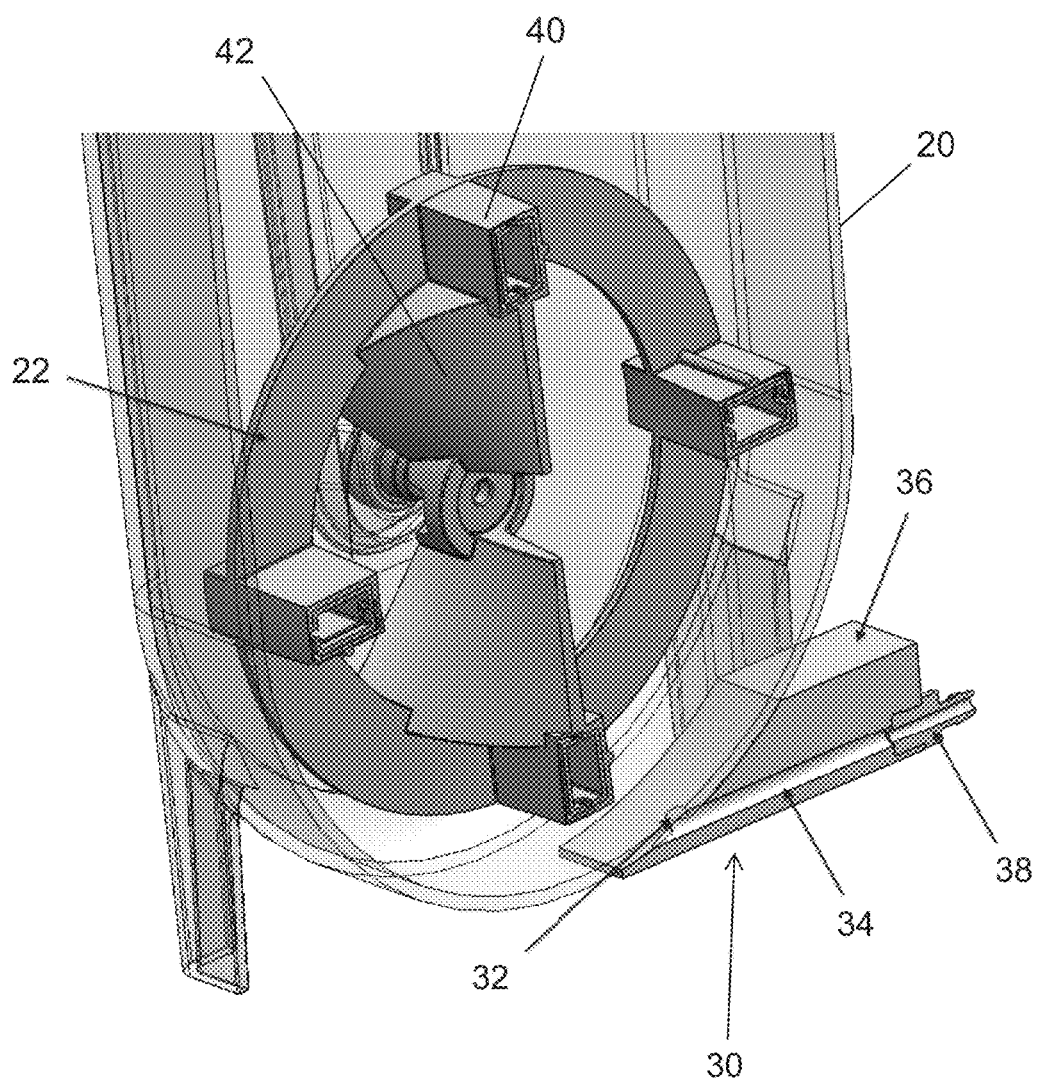
FIG. 2 is a close-up sectional view of a dispensing portion of the mixer.

One embodiment of this invention, as depicted in FIG. 1, consists of a vessel 20 defined by outer walls 21 to hold the chilled cells and excipient and an impeller 22 enclosed within the vessel for maintaining cells in suspension. The outer walls 21 include a lower curved wall 23. The impeller 22 is positioned in a lower portion of the sterile containment vessel and oriented in a vertical plane and rotates about a horizontal axis 24 to allow maximum particle suspension at minimum power input and reduce shear effects on cells. Cells and excipient are introduced into the vessel by removing a threaded port cap 26 in a Class 100 clean room environment or equivalent, and then transferring the content into the vessel 20 via pipetting or pouring. The cap 26 may be threaded back onto the port to seal prior to cell dispensing to minimize potential for introducing foreign materials. A hydrophobic membrane 28 on the cap 26 allows improved thermal exchange with the air in the cold room to help maintain temperature.

During cell dispensing, fluid is removed at a lower dispenser 30 via a vessel orifice 32 that extends through an outer wall near the bottom of the vessel 20. The fluid travels down a bore 34 in a machined block 36 of the dispenser 30 which is affixed to the vessel 20 and sealed around the orifice 32. A hose barb adaptor 38 open to the bore 34 that mates with the machined block 36 allows tubing to be secured to it to maintain a sterile fluid path. Prior to sterilization of this device, tubing would be attached and secured to the hose barb adaptor 38 and terminated with another adaptor depending on how the user wishes to connect it to a dosing pump (not shown).

The impeller 22 consists of a plurality of paddles 40 along its outer periphery that generate strong sweeping motion of the liquid as it rotates to counteract cell settling in the excipient. The paddles 40, which are hollow, can encapsulate permanent magnets 41, which are used to couple with magnets on the agitation controller (not shown) to drive the rotation of the impeller 22. The impeller 22 also consists of two diametrically-opposed vanes 42 extending from the paddles to an inner hub that create bi-axial fluid flow as the impeller rotates to ensure homogeneity of cells suspended in the excipient. That is, the vanes 42 have curved surfaces that urge flow axially when the impeller is rotated in one direction.

Desirably, there is a minimum of one port for adding cells and excipient into the vessel and a minimum of one port for dispensing the cells and excipient, both of which could be sealed as needed to prevent foreign contaminants, biological or not, from contacting the cell product. The dispensing port should allow for flexibility by the user to specify how to connect the device to a dosing pump—either by using an aseptic connector (GE ReadyMate Disposable Aseptic Connector, Pall Kleenpak™ Sterile Connector, or equivalent), a dead-ended thermoplastic tubing that may be heat welded onto another dead-ended thermoplastic tubing, or tubing that is terminated with fittings that may be connected to another tubing inside a Class 100 clean room environment. The dosing pump would be a calibrated instrument to allow accurate metering of liquid dispensed into vials.

Since 2-8° C. temperature would be maintained in the vessel either by placing the mixing device in a cold room or a refrigerator or by applying cold packs, the vessel wall would therefore be composed of material and at thickness that allows relatively high thermal transfer. If the addition port is positioned at the top of the vessel, the cap on the port could further contain a hydrophobic, sterilizing-grade (0.22-micron or finer) membrane to allow gas exchange with chilled gas in the cold room or refrigerator for improved thermal transfer. Additionally, the material could be clear in appearance to allow visual confirmation of impeller rotation and cell suspension.

All of the components of this mixing device that come in contact with the chilled excipient and cells should be manufactured from medical-grade materials that have been certified to USP Class VI, ISO 10993, or equivalent, to ensure they meet the regulatory requirements of the user. The mixing device would also need to be sterilizable to ensure Sterility Assurance Level (SAL) of $10^{-6}$—either by gamma radiation, steam sterilization, or other applicable means.

It is understood that the foregoing examples are considered illustrative only of the principles of the invention. Further, since numerous modifications and changes will readily occur to those skilled in the art, it is not desired to limit the invention to the exact construction and operation shown and, accordingly, all suitable modifications and equivalents may be resorted to, falling within the scope of the invention.

What is claimed is:

1. A cell dispensing device, comprising:
    a sterile containment vessel having
        i. outer walls including a lower curved wall located at a lower end of the vessel,
        ii. an upper inlet through one of the outer walls including a threaded port cap containing a vent and a hydrophobic membrane configured to permit thermal exchange with an external environment outside the vessel,
        iii. a mixer in the sterile containment vessel configured to rotate about a horizontal axis and positioned in a lower portion of the sterile containment vessel so as to stir contents of the sterile containment vessel adjacent the lower curved wall, and
        iv. an orifice in the lower curved wall; and
    a dispenser sealingly attached to the lower curved wall of the sterile containment vessel in fluid communication with the orifice for dispensing quantities of suspended cells having a homogeneous cell distribution, the dispenser including a machined block affixed to the sterile containment vessel and sealed around the orifice having a bore in fluid communication with the orifice and an outlet port in fluid communication with the bore, the outlet port being configured to connect to tubing.

2. The cell dispensing device of claim 1, wherein the hydrophobic membrane is a sterilizing-grade 0.22-micron or finer membrane.

3. The cell dispensing device of claim 1, wherein the mixer is an impeller which has a plurality of paddles along an outer periphery thereof.

4. The cell dispensing device of claim 3, wherein the plurality of paddles include encapsulated magnets configured to couple paddles encapsulate magnets for coupling to magnets on a rotational drive mechanism external to the sterile containment vessel.

5. The cell dispensing device of claim 3, wherein the impeller includes two diametrically-opposed vanes extending radially inward from the two of the plurality of paddles, the two diametrically-opposed vanes being configured to create bi-axial fluid flow as the impeller rotates.

6. The cell dispensing device of claim 3, wherein the plurality of paddles are hollow.

7. The cell dispensing device of claim 6, wherein the impeller includes two diametrically-opposed vanes extending from the plurality of paddles to an inner hub that create bi-axial fluid flow as the impeller rotates.

8. The cell dispensing device of claim 1, wherein the dispenser outlet port is a hose barb adaptor.

9. A method of dispensing cells using the cell dispensing device of claim 1, including introducing cells and excipient into the sterile containment vessel via the upper inlet, rotating the mixer, and withdrawing cells from the sterile containment vessel through the dispenser and out of the outlet port.

10. The method of claim 9, further including maintaining a temperature of the cells and excipient at 2-8° C. during the steps of introducing, rotating and withdrawing.

11. The method of claim 10, further including placing the sterile containment vessel in a cold room or refrigerator to maintain the temperature of the cells and excipient.

12. The method of claim 10, further including applying cold packs to the sterile containment vessel to maintain the temperature of the cells and excipient.

13. The method of claim 9, wherein the mixer is an impeller having has permanent magnets mounted thereon configured to couple thereon for coupling to magnets on a rotational drive mechanism external to the sterile containment vessel, the method including rotating the impeller with the rotational drive mechanism.

14. The method of claim 9, wherein the mixer is an impeller which has a plurality of hollow paddles along an outer periphery.

15. The method of claim 14, wherein the impeller includes vanes that create bi-axial fluid flow as the impeller rotates.

16. The method of claim 9, wherein prior to the step of withdrawing cells through the dispenser the method includes connecting a dosing pump to the outlet port, and the method further includes calibrating the dosing pump for accurate metering of cells in liquid into vials.

17. The method of claim 16, wherein the outlet port is selected from the group consisting of an aseptic connector, a dead-ended thermoplastic tubing, and tubing that is terminated with a fitting that may be connected to another tubing inside a Class 100 clean room environment.

\* \* \* \* \*

UNITED STATES PATENT AND TRADEMARK OFFICE
CERTIFICATE OF CORRECTION

PATENT NO. : 10,323,223 B2  
APPLICATION NO. : 15/413077  
DATED : June 18, 2019  
INVENTOR(S) : Chanyong Brian Lee et al.

Page 1 of 1

It is certified that error appears in the above-identified patent and that said Letters Patent is hereby corrected as shown below:

In the Claims

At Column 4, Line 24, "couple paddles encapsulate magnets for coupling to" should be -- couple to --.

At Column 4, Line 56, "having has" should be -- having --.

At Column 4, Line 57, "couple thereon for coupling to" should be -- couple to --.

Signed and Sealed this  
Fifteenth Day of September, 2020

Andrei Iancu  
*Director of the United States Patent and Trademark Office*